United States Patent [19]

Alt

[11] Patent Number: 5,523,416

[45] Date of Patent: Jun. 4, 1996

[54] PROCESS FOR PREPARING 3-(4-AMINOETHOXY-BENZOYL) BENZO (B)-THIOPHENES

[75] Inventor: Charles A. Alt, Greenwood, Ind.

[73] Assignee: Eli Lilly and Company, Indianapolis, Ind.

[21] Appl. No.: 422,294

[22] Filed: Apr. 14, 1995

Related U.S. Application Data

[62] Division of Ser. No. 279,456, Jul. 22, 1994, abandoned.

[51] Int. Cl.$^6$ .................... C07D 333/58; C07D 333/56
[52] U.S. Cl. .................................. 549/57; 549/51
[58] Field of Search .................... 549/57, 51, 49

[56] References Cited

U.S. PATENT DOCUMENTS

| | | | |
|---|---|---|---|
| 4,233,333 | 11/1980 | Trummlitz et al. | 426/548 |
| 4,436,748 | 3/1984 | Ong et al. | 424/275 |
| 5,292,894 | 3/1994 | Ebel et al. | 549/43 |
| 5,298,630 | 3/1994 | Kagano et al. | 549/57 |
| 5,403,939 | 4/1994 | Yazawa et al. | 549/57 |
| 5,426,191 | 6/1995 | Walker | 549/57 |

OTHER PUBLICATIONS

Campaigne E., "Thiophenes and their Benzo–Derivatives: (III), Synthesis and Applications", Comprehensive Heterocyclic Chemistry, vol. 4, Part 3, pp. 863–894, (1984).

*Primary Examiner*—Richard L. Raymond
*Assistant Examiner*—Deborah Lambkin
*Attorney, Agent, or Firm*—James J. Sales

[57] ABSTRACT

The invention provides a process for preparing 6-alkoxy-3-(4-alkoxyphenyl)benzo[B]thiophenes in good yield on a manufacturing scale without generating a thick, potentially yield-reducing, paste. The invention also provides methods for converting a-(-alkoxyphenylthio)-4-alkoxyacetophenones into 6-hydroxy-2-(4-hydroxyphenyl)-3-[4-(2-aminoethoxy)benzoyl]benzo[B]thiophenes via acylation of a dialkoxy benzo[B]thiophene. Each of these preparations relies on an intramolecular cyclization of a dialkoxy acetophenone derivative to yield a benzo[B]thiophene without generating a thick paste that lowers overall yields on a manufacturing scale.

5 Claims, No Drawings

PROCESS FOR PREPARING 3-(4-AMINOETHOXY-BENZOYL) BENZO (B)-THIOPHENES

This application is a division of application Ser. No. 08/279,456, filed Jul. 22, 1994, abandoned.

BACKGROUND OF THE INVENTION

This invention relates to the field of pharmaceutical chemistry, and provides an advantageous process for preparing group of 6-hydroxy-2-(4-hydroxyphenyl)-3-[4-(2-aminoethoxy)benzoyl]benzo[B]thiophenes. In particular, the invention relates to an improved process for preparing intermediates, i.e., dialkoxy benzo[B]thiophenes, useful for preparing such thiophenes. The process provides the desired compounds in excellent yield on a large scale without mixing problems.

The preparation of 6-hydroxy-2-(4-hydroxyphenyl)-3-[4-( 2-aminoethoxy)benzoyl]benzo[B]thiophenes through a dialkoxy benzo[B]thiophene intermediate was described in U.S. Pat. No. 4,380,635. The process described in that patent relies on the intramolecular cyclization of α-(3-methoxyphenyl-thio)-4-methoxyacetophenone in polyphosphoric acid (PPA). Heating the acetophenone starting material in PPA at about 85° C. for about 1 hour provides an approximately 3:1 mixture of two isomers, 6-methoxy-2-(4-methoxyphenyl)benzo[B]thiophene and 4-methoxy-2-( 4-methoxyphenyl)benzo[B]thiophene. When this transformation is conducted on a manufacturing scale, the isomeric benzo[B]thiophenes precipitate and produce a thick paste that cannot be stirred adequately in conventional manufacturing equipment.

Use of a solvent to alleviate the problem caused by a paste in a different reaction scheme has been attempted by Guy et al., *Synthesis*, 222 (1980). However, when this approach is applied to the instant scheme, the addition of a solvent results in incomplete cyclization of the starting acetophenone, incomplete rearrangement of 6-methoxy-3-(4-methoxyphenyl)benzo[B]thiophene, and dramatically increased reaction times. Thus, there is a need for a method to convert α-(-methoxyphenylthio)-4-methoxyacetophenone into 6-methoxy-3-( 4-methoxyphenyl)benzo[B]thiophene in suitable yield in acceptable reaction times without generating a paste that prevents adequate mixing of the reaction mixture.

Most of the compounds prepared by the process of this invention are taught in U.S. Pat. No. 4,133,814, incorporated herein by reference.

SUMMARY OF THE INVENTION

The invention provides a process for preparing 6-alkoxy-3-( 4-alkoxyphenyl)benzo[B]thiophenes in good yield on a manufacturing scale without generating a thick, potentially yield-reducing, paste. The invention also provides methods for converting α-(-alkoxyphenylthio)-4-alkoxyacetophenones into 6-hydroxy-2-(4-hydroxyphenyl)-3-[4-( 2-aminoethoxy)benzoyl] benzo[B]thiophenes via acylation of a dialkoxy benzo[B]thiophene. Each of these preparations relies on an intramolecular cyclization of a dialkoxy acetophenone derivative to yield a benzo[B]thiophene without generating a thick paste that lowers overall yields on a manufacturing scale.

Thus, this invention provides a process for preparing a compound of formula I

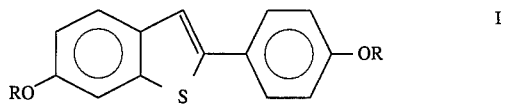

wherein the R groups are the same or different and represent $C_1$—$C_6$ alkyl;
comprising cyclizing a compound of formula II

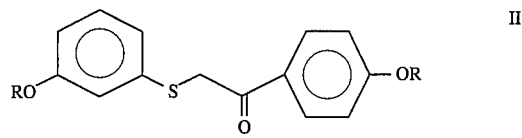

where the R groups are defined as above, with polyphosphoric acid in the presence of phosphoric acid.

The invention also encompasses methods for preparing a compound of formula III

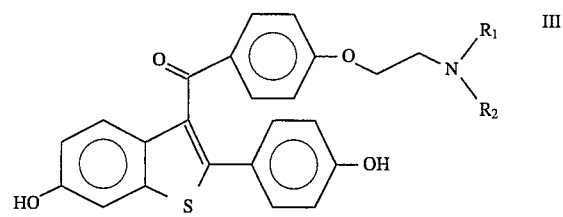

wherein $R_1$ and $R_2$ are independently $C_1$–$C_4$ alkyl, or combine to form $C_4$–$C_6$ polymethylene or —($CH_2$—)$_2$O($CH_2$)$_2$—; which process comprises:
cyclizing a compound of formula II with polyphosphoric acid in the presence of phosphoric acid to yield a mixture of alkoxy-2-(4-alkoxyphenyl)benzo-[B]thiophenes;
optionally removing the alkoxy groups and subsequently reprotecting the hydroxy groups;
acylating the hydroxy-protected benzo[B]thiophenes under Friedel-Crafts conditions with an acylating agent of the formula

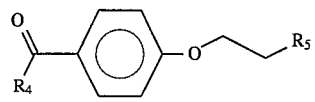

wherein $R_5$ is X or

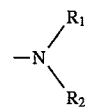

X is chloro, bromo, an active ester, or —SO2R3;
and $R_4$ is chloro, bromo, iodo, or an activating ester group; when $R_5$ is X, displacing the X group with an amine of the formula

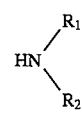

and cleaving the hydroxy protecting groups.

DETAILED DESCRIPTION OF THE INVENTION

In this document, all temperatures will be stated in degrees Celsius. All amounts, ratios, concentrations, proportions and the like will be stated in weight units, unless otherwise stated, except for ratios of solvents, which are in volume units.

In the formulas above the general terms bear their usual meanings. For example, the term $C_1$–$C_4$ primary or secondary alkyl refers to groups such as methyl, ethyl, propyl, s-butyl, i-butyl and the like. The term $C_1$–$C_4$ alkyl includes the above groups and also includes t-butyl. The term $C_1$–$C_4$ alkoxy refers to straight or branched chain lower alkoxy groups such as methoxy, ethoxy, propoxy, isopropoxy, butyloxy and the like. The term $C_4$–$C_6$ polymethylene refers to tetramethylene, pentamethylene and hexamethylene. The term $C_1$–$C_6$ alkyl includes the $C_1$–$C_4$ groups described above and various straight or branched chain pentyl and hexyl groups.

The term "substituted phenyl" refers to a phenyl molecule having one or two substituents selected from the group consisting of $C_1$–$C_4$ alkyl, $C_1$–$C_5$ alkoxy, hydroxy, nitro, chloro, fluoro, or tri(chloro or fluoro)methyl. "$C_1$–$C_5$ alkoxy" represents a $C_1$–$C_5$ alkyl group attached through a carbon bridge such as, for example, methoxy, ethoxy, n-propoxy, isopropoxy, and the like.

The following group of representative products of the process and of this invention will be mentioned, to assure that the reader fully understands the overall purpose of the process:

6-hydroxy-2-(4-hydroxyphenyl)-3-[4-( 2-dimethylaminoethoxy)-benzoyl]benzo [B]thiophene;

3-[4-(2-ethoxymethylaminoethoxy)benzoyl]-6-hydroxy-2-( 4-hydroxylphenyl)benzo[B]thiophene;

3-[4-(2-ethoxylisopropylaminoethoxy)benzoyl]-6-hydroxy-2-( 4-hydroxyphenyl))benzo[B]thiophene;

3-(4-(2-dibutylaminoethoxy)benzoyl]-5-hydroxy-2-( 4-hydroxyphenyl)benzo[B]thiophene;

3-[4-(2-(1-methylpropyl)methylaminoethoxy]-benzoyl]-6-hydroxy-2-(4-hydroxyphenyl)benzo[B]thiophene;

6-hydroxy-2-(4-hydroxyphenyl)-3-[4-[2-di( 2-methylpropyl)aminoethoxy]benzoyl]benzo[B]thiophene;

6-hydroxy-2-(4-hydroxyphenyl)-3-[4-( 2-pyrrolidinoethoxy)benzoyl]benzo [B]thiophene;

6-hydroxy-2-(4-hydroxyphenyl)-3-[4-( 2-piperidinoethoxy) benzoyl]benzo[B]thiophene;

6-hydroxy-2-(4-hydroxyphenyl)-3-[4-( 2-morpholinoethoxy)benzoyl]benzo[B]thiophene;

3-[4-(2-hexamethyleneiminoethoxy)benzoyl]-6-hydroxy-2-(4-hydroxyphenyl)benzo[B]thiophene.

The compounds are tissue specific estrogenic agonist/antagonists and, thus, are useful for estrogenic, antiestrogenic and antiandrogenic therapy. Accordingly, they are useful in treating pathological conditions of endocrine target organs, which conditions are dependent or partially dependent on an estrogen or on an androgen. Such conditions include mammary cancer, mammary fibrocystic disease, cancer of the prostate, and benign prostatic hypertrophy.

U.S. Pat. No. 4,131,814 teaches that certain of the compounds are also useful as anti-cancer and anti-fertility drugs. The antiestrogenic and antiandrogenic efficacy of a preferred compound prepared by this invention, 6-hydroxy-2-( 4-hydroxyphenyl)-3-[4(2-Piperidinoethoxy)benzoyl]benzo[B] thiophene, is explained in further detail in U.S. Pat. No. 4,413,068.

The dose of a compound to be administered to a human is rather widely variable. It should be noted that it may be necessary to adjust the dose of a compound when it is administered in the form of a salt, such as a laurate, the salt-forming moiety of which has an appreciable molecular weight. The general range of effective administration rates of the compounds is from about 0.05 mg/kg/day to about 50 mg/kg/day. A preferred rate range is from about 0.1 mg/kg/day to about 10 mg/kg/day, and the most highly preferred range is from about 0.1 mg/kg/day to about 5 mg/kg/day. Of course, it is often practical to administer the daily dose of a compound in portions at various hours of the day.

The route of administration of the compounds is not critical. The compounds are known to be absorbed from the alimentary tract, and so it is usually preferred to administer a compound orally for reasons of convenience. However, the compounds may equally effectively be administered percutaneously, or as suppositories for absorption by the rectum, if desired in a given instance.

The compounds are usually administered as pharmaceutical compositions. All of the usual types of compositions may be used including tablets, chewable tablets, capsules, solutions, parenteral solutions, troches, suppositories and suspensions. Compositions are formulated to contain a daily dose, or a convenient fraction of a daily dose, in a dosage unit, which may be a single tablet or capsule or a convenient volume of a liquid. In general, compositions contain from about 0.000006% to about 60% of compound, depending on the desired dose and the type of composition to be use.

The activity of the compounds does not depend on the composition in which it is administered or on the concentration of the composition. Thus, the compositions are chosen and formulated solely for convenience and economy.

The process of this invention is preferably used for preparing intermediates of formula I which are subsequently acylated to form compounds of formula III where $R_1$ and $R_2$ combine to form tetramethylene or pentamethylene.

The compounds of formula I are prepared according to the invention by cyclizing an a-(-alkoxyphenylthio)-4-alkoxyacetophenone in a mixture of polyphosphoric acid (PPA) and phosphoric acid (H3PO$_4$) to form a mixture of 6-alkoxy-2-(4-alkoxyphenyl)benzo[B]thiophene (I) and 4-alkoxy-2-(4-alkoxyphenyl)benzo[B]thiophene, as is depicted in Scheme I.

Conversion of 6-alkoxy-2-(4-alkoxyphenyl)benzo[B] thiophene to compounds of formula III may be accomplished according to the reactions outlined in Schemes II and III, as is more fully explained below.

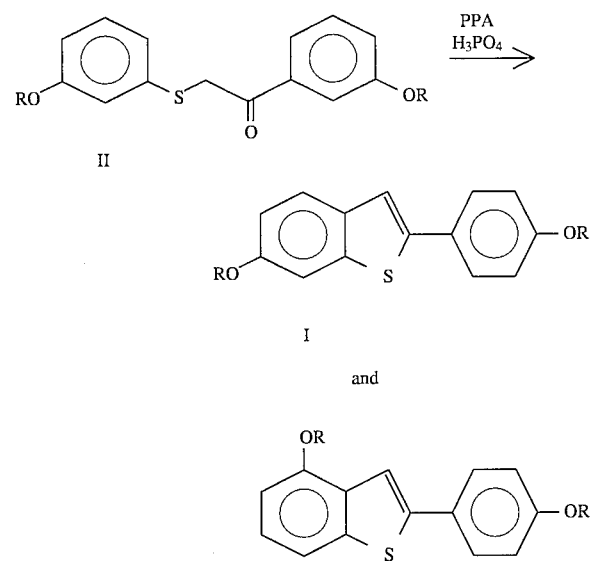

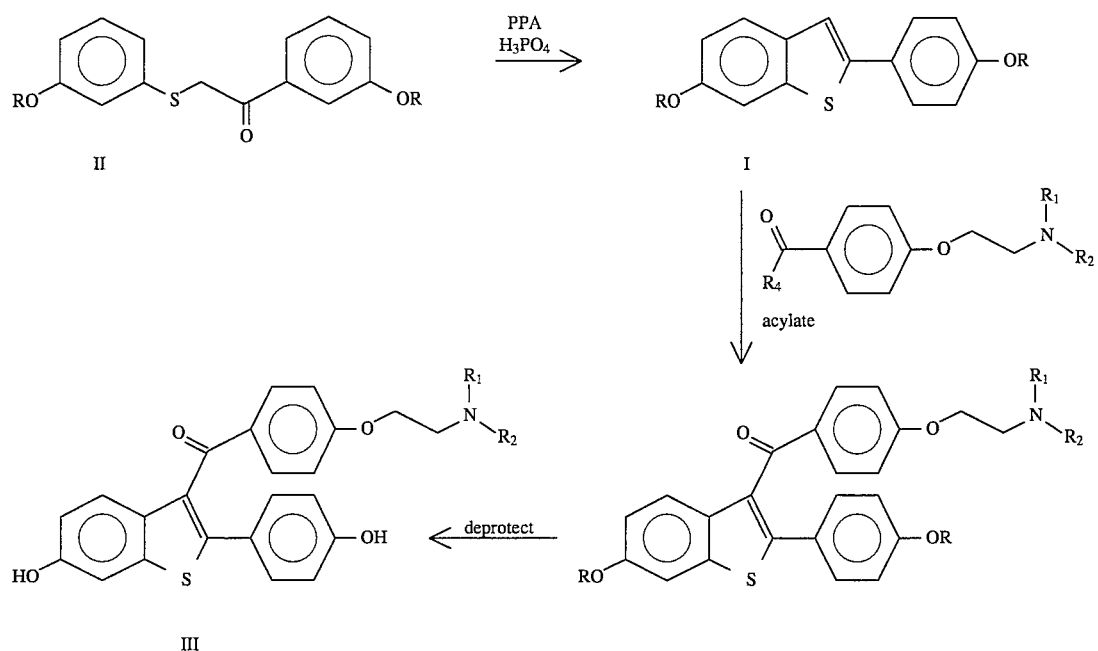
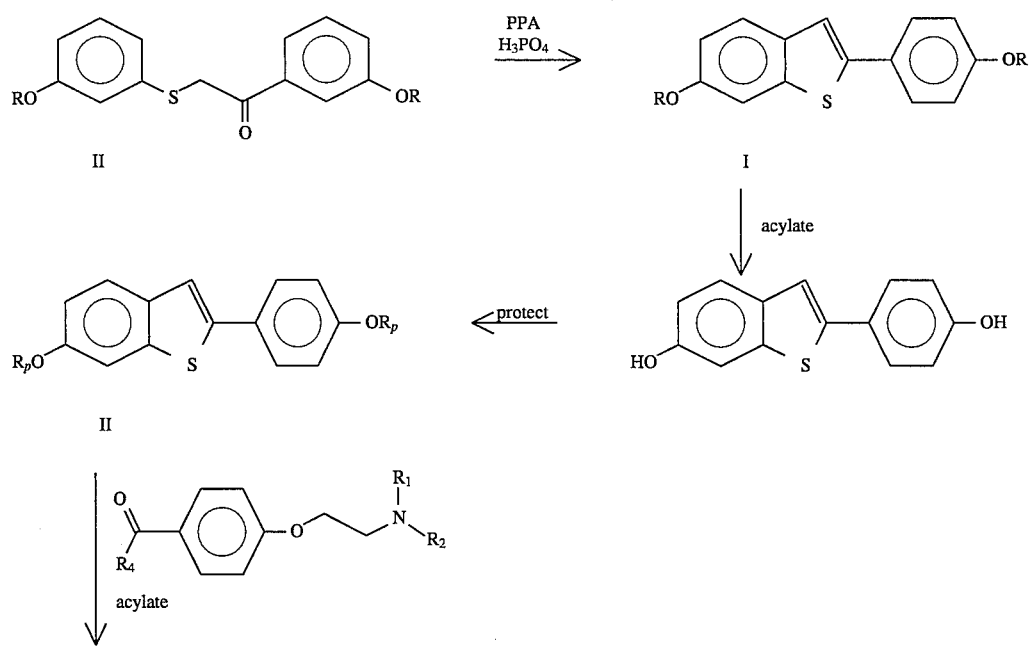

-continued
SCHEME III

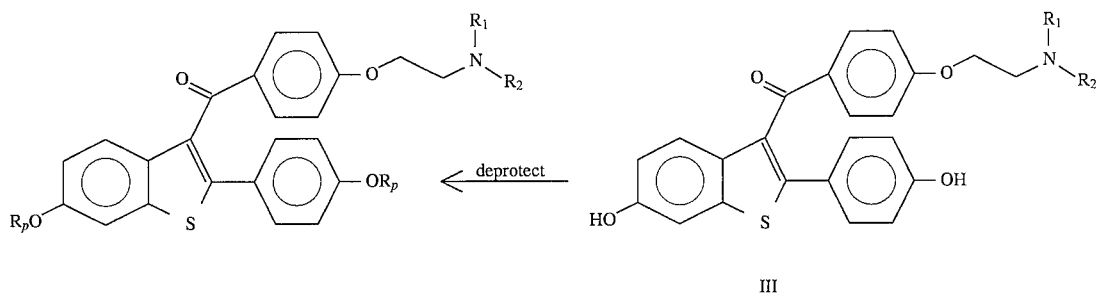

III

In Scheme III, R, $R_1$, R2, and $R_4$ are defined as above, and $R_p$ represents —$COR_3$ or —$SO_2R_3$, and $R_3$ is $C_1$-$C_4$ primary or secondary alkyl, trifluoromethyl, trichloromethyl, phenyl, p-tolyl, p-anisyl, or mono- or di(halo or nitro)phenyl.

As is described in Scheme II, dialkoxybenzo[B]thiophene may be acylated with the acylating agent described above, and the protecting group removed to afford compound III. Alternatively, as shown in Scheme III, subsequent to intramolecular cyclization of acetophenone II, the alkoxy groups of the dialkoxybenzothiophene may be removed to yield a dihydroxybenzothiophene. The hydroxy groups may then be reprotected and the resulting protected dihydroxy compound may then be reacted with the acylating agent described above, after which the protecting groups are removed.

Polyphosphoric Acid Cyclization

The cyclization of a-(-alkoxyphenyl-thio)-4-alkoxyacetophenone is carried out in polyphosphoric acid (PPA) with phosphoric acid to yield 6-alkoxy-2-(4-alkoxyphenyl)benzo[B]thiophene and 4-alkoxy-2-(4-alkoxyphenyl)benzo[B]thiophene. The reaction proceeds cleanly without generation of a thick, difficult-to-stir paste.

According to the invention, the cyclization is conducted at temperatures of from about 50° to 110° C., preferably from about 75° to 95° C., and most preferably from about 80° to 90° C. The acetophenone starting material is heated in the PPA/$H_3PO_4$ mixture for at least 30 minutes, and preferably from about 60 to 180 minutes. As presently practiced, the acetophenone is cyclized at about 85° C. for about 1.75 hours. The weight ratio of PPA to $H_3PO_4$ in this cyclization reaction is from about 10:1 to 1:1.

Subsequent to this initial heating period, the reaction is cooled to a temperature of from about 25° to 75° C., and preferably to about 40° to 60° C., at which time sufficient water or ice is added to destroy the remaining PPA and precipitate the dialkoxybenzo[B]thiophene. The addition of water is substantially exothermic.

The benzo[B]thiophene may be isolated with a standard aqueous workup by adding an organic solvent, separating the aqueous layers, optionally extracting the aqueous layer again with the organic solvent, combining the organic layers, and concentrating the combined organic layers. When the starting material is the methoxy derivative, the desired 6-alkoxy compound crystallizes in the concentrated solvent while the 4-alkoxy isomer remains in solution. The desired 6-alkoxy compound may be collected, preferably by filtration. Yields approaching 70% may be realized with this process.

The organic solvents suitable for use in the workup of inventive process include diethyl ether, ethyl acetate and aromatic hydrocarbons, such as, for example, benzene, and toluene.

In a preferred cyclization process according to the invention, the starting acetophenone is a-(-methoxyphenylthio)-4-methoxyacetophenone which yields, upon workup after cyclization, 6-methoxy-2-(4-methoxyphenyl)benzo[B]thiophene. This material may subsequently be converted into 6-hydroxy-2-( 4-hydroxyphenyl)-3-[4-(2-aminoethoxy)benzoyl]benzo[B]thiophene, as indicated above and more fully explained below.

Dealkylation

In processes where the hydroxy groups of the dialkoxybenzo[B]thiophene are dealkylated and reprotected, the deprotection may be effected with, for example, a tertiary amino hydrochloride such as pyridine hydrochloride at elevated temperature. The deprotected diol may be recovered by cooling the mixture, and isolating the diol after aqueous workup.

Reprotection

When the benzo[B]thiophene is converted according to Scheme III, the —$COR_3$ and —$SO_2R_3$ groups are placed on the deprotected dihydroxy compound according to methods known in the art. For example, when a —$COR_3$ group is desired, the dihydroxy compound is reacted with an agent such as an acyl chloride, bromide, cyanide or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine or the like. The reaction may also be carried out in an inert solvent such as ethyl acetate, dimethylformamide, dimethylsulfoxide, dioxane, dimethoxyethane, acetonitrile, acetone, methyl ethyl ketone or the like, to which at least one equivalent of an acid scavenger, such as a tertiary amine, has been added. Acylation catalysts such as 4-dimethylaminopyridine or 4pyrrolidinopyridine may be used, if desired. See, in general, Haslam, *Tetrahedron* 36:2429–33 (1980). The acylation reactions which provide —$COR_3$ groups are carried out at moderate temperatures in the range of from –25° to 100°.

Such acylations of the hydroxy groups may also be performed by acid-catalyzed reactions of the appropriate carboxylic acids, in inert organic solvents or neat. Acid catalysts such as sulfuric acid, polyphosphoric acid, methanesulfonic acid and the like are used.

The —$COR_3$ groups may also be provided by forming an active ester of the appropriate acid, such as the esters formed by such known reagents as dicyclohexylcarbodiimide, acylimidazoles, nitrophenols, pentachlorophenol, N-hydroxysuccinimide and 1-hydroxybenzotriazole. See, for example, *Bul. Chem. Soc. Japan* 38:1979 (1965), and *Chem. Ber.* 788 , 2024 (1970).

Other techniques are also know, such as by means of mixed anhydrides of the phosphorus compounds, Shioiri and Hamada, *J. Org. Chem* 43:3631–32 (1978), the use of 2-haloheterocyclic compounds such as 2-chloropyridine, Narasaka et al., *Chem. Let.* 763–66 (1977); and the use of thiol esters.

All of the above techniques which provide $-COR_3$ groups are carried out in solvents as discussed above. Those techniques which do not produce an acid product in the course of the reaction, of course, do not call for an acid scavenger in the reaction mixture.

Still other methods are also useful, such as the use of an $R_3$-substituted ketene in an inert solvent, as discussed above, at a low temperature in the range of $-30°$ to $25°$. Still further, the dihydroxy compound can be first converted to its dianion by treatment with a very strong base such as sodium hydroxide, sodium methoxide, potassium hydride, sodium hydride, n-butyllithium or the like, in order to obtain more complete reaction with the reagents which have been mentioned above. Protection by the dianion technique is carried out in an inert solvent as described above, with no additional base or catalyst. The temperature of reactions according to the dianion technique is from $-30°$ to $50°$ C.

When a $-SO_2R_3$ protected compound is desired, the dihydroxy starting compound is reacted with, for example, a derivative of the appropriate sulfonic acid, such as sulfonyl chloride, bromide or sulfonyl ammonium salt, as taught by King and Manoir, *J. Am. Chem. Soc.* 97:2566–67 (1975). The dihydroxy compound can also be reacted with the appropriate sulfonic anhydride. Such reactions are carried out under conditions such as were explained above in the discussion of reactions with acyl halides and the like.

The $-SO_2R_3$ groups may also be provided by reaction of the dihydroxy compound with an appropriately substituted sulfene under conditions as discussed above for reactions with substituted ketenes. Still further, any of the sulfonate-producing reactions may be carried out on a dihydroxy compound in the dianion form, as discussed above.

The preferred protected starting compounds are those wherein the protecting group, R, is methanesulfonyl, p-toluenesulfonyl, acetyl, benzoyl, p-anisoyl and benzenesulfonyl. Other classes of preferred protecting groups include those wherein R is $COR_3$, wherein R is $-SO_2R_3$, wherein $R_3$ is $C_1$–$C_4$ primary or secondary alkyl; and wherein $R_3$ is phenyl, p-tolyl, p-anisyl or mono- or di(halo or nitro)phenyl.

Acylation

Acylation of the protected starting compound according to Schemes II or III can be done with either an acylating agent already containing the aminoethoxy group of the desired product or with a precursor of it. The acylating agents are discussed in detail below.

The acylation is a Friedel-Crafts acylation, and is carried out in the usual way. Either a Lewis acid or a proton acid may be used as the Friedel-Crafts catalyst; an excellent discussion of such catalysts appears in Olah, Friedel-Crafts and Related Reactions, Interscience Publ., New York, London and Sidney, 1963, Vol. I, Ch. III and IV.

As explained by Olah, the classical Friedel-Crafts catalysts were Lewis acids. Such metal halides as aluminum chloride, aluminum bromide, and chloride, boron trifluoride, boron trichloride, boron tribromide, titanium tetrachloride, titanium tetrabromide, stannic chloride, stannic bromide, bismuth trichloride and ferric chloride are well known catalysts and are useful in this acylation. The proton acid catalysts are also useful for this acylation, and include such substances as phosphoric acid, polyphosphoric acid, perchloric acid, chlorosulfonic acid, alkylsulfonic acids such as methanesulfonic and ethanesulfonic acids, toluenesulfonic and benzenesulfonic acids, sulfuric acid, chloroacetic acid and trifluoroacetic acid. It is preferred to carry out the acylation with aluminum chloride or trifluoromethanesulfonic acid.

The acylation is ordinarily carried out in a solvent, and any inert organic solvent which is not significantly attacked by the conditions may be used. For example, halogenated solvents such as dichloromethane, 1,2-dichloromethane, chloroform and the like may be used, as can aromatics such as benzene, chlorobenzene and the like, alkanes such as petroleum ether, hexane and the like, and nitrohydrocarbons such as nitrobenzene and nitroalkanes.

It has been found that toluene is rather easily acylated under the conditions used in the Friedel-Crafts acylation step, and so it is important, when toluene is used in an earlier step of the process, to remove it as completely as possible from the protected starting compound, to avoid wasting the acylating agent.

The acylations may be carried out at temperatures from about the ambient temperature to about 100° preferably at the reflux temperature of the reaction mixture for processes catalyzed by the preferred proton acid catalyst, trifluoromethanesulfonic acid, and preferably at about ambient temperature for Lewis acid catalyzed processes.

The acylating agent is an active form of the appropriate benzoic acid, wherein $R_4$ is one of the recognized "active groups", such as chlorine atom, a bromine atom, or an activating ester. Appropriate activating esters are formed with hydroxybenzotriazole, acylimidazoles, nitrophenols, pentachlorophenol, N-hydroxysuccinimide, dicyclohexylcarbodiimide and the like. The group $R_4$ may also indicate an anhydride, especially a mixed anhydride such as those formed with small carboxylic acids such as acetic acid, formic acid and especially sulfonic acids.

The preferred acylating agents are those wherein $R_4$ is chloro or bromo. Thus, the most highly preferred individual acylating agents are 4-(2-piperidinoethoxy)benzoyl chloride, 4-(2-pyrrolidinoethoxy)benzoyl bromide, 4-(2-pyrrolidinoethoxy)benzoyl chloride, 4-(2-pyrrolidinoethoxy)benzoyl bromide, 4-[2-(3-methylpyrrolidino)ethoxy]benzoyl chloride and 4-[2-(3-methylpyrrolidino)ethoxy]benzoyl bromide.

It is preferred, when the basic side chain is added as part of the acylating agent to use as the acylating agent a small excess (1.05–1.5 molar) of the proper benzoyl halide, and to use, as the Friedel-Crafts catalyst, a slight molar excess of trifluoromethanesulfonic acid, or, alternatively, fluorosulfonic acid, p-toluenesulfonic acid, a dihalophosphoric acid or concentrated sulfuric acid. Alternatively, the reaction is also carried out in a preferred manner by using a substantial excess (1.5 to 3.5 molar) of the benzoyl halide in the presence of a large excess (2–12 molar) of aluminum chloride; other Lewis acid catalysts, such as aluminum bromide and the like may also be used.

In the case of acylations employing an aminoethoxy precursor, it is preferred to carry out the acylation in the presence of a strong acid such as was discussed immediately above. In this reaction, a full equivalent of acid is not necessary; a catalytic amount of acid is adequate. It is preferred to carry out the acylation steps in an inert halogenated solvent such as chloroform, dichloromethane, benzene, 1,2-dichloroethane and the like. In general, see as to such acylation reactions an article by Effenberger, *Angew. Chem. Int. Ed. Engl.* 19:151–230 especially 163–165 (1980).

Displacement

When the starting compound is acylated with an aminoethoxy precursor, the amino group of the product is subsequently put in place by displacing the X group with the appropriate secondary amine. The X groups are leaving groups, preferably chloro or bromo, which are easily displaced by an amine according to known methods.

For example, the displacement is carried out in an inert solvent such as ketones in the nature of acetone or methyl ethyl ketone, esters such as ethyl acetate and propyl formate, alcohols such as methanol or ethanol, nitriles such as acetonitrile, or amides such as dimethylacetamide and dimethylformamide, or in such inert solvents as hexamethylphosphoramide, and in the presence of an acid scavenger such as alkali metal carbonates and bicarbonates and the like. At least an equimolar quality of acid scavenger is needed, and preferably a moderate excess. The displacement is carried out at ambient temperature, or may be carried out at moderately elevated temperatures from about ambient temperature to the reflux temperature of the reaction mixture.

More preferably, the displacement may be carried out in the additional presence of a catalytic amount of iodide ion, which acts as a catalyst for the displacement. When iodide is used in the mixture, the temperature range is lower, from about 0° to, preferably, the ambient temperature, although elevated temperatures are possible in some instances.

Further, the anion of the amine may be formed before the reaction is carried out, as by contact with a very strong base such as sodium hydride or an alkyl-lithium compound. The use of an anion does not otherwise change the manner in which the displacement is carried out, except that an acid scavenger is not needed.

Deprotection of Preprotected Dihydroxythiophenes

A dihydroxy compound is obtained by cleaving the protecting groups R, from the acylated compounds (see Scheme III). Both —COR$_3$ and —SOR$_3$-protected compounds have been deprotected by simple hydrolysis with strong or moderately strong bases. For example, bases such as alkali metal hydroxides may be used for the hydrolysis, at temperatures from about the ambient temperature to about 100°. At least two equivalents of base are needed, of course. Such hydrolyses are conveniently carried out in hydroxylic solvents, especially aqueous alkanols. The reactions may be also carried out however, in any convenient solvent which lends itself to hydrolysis reactions, such as polyols including ethylene glycol ethers, such as tetrahydrofuran and the like, ketones such as acetone and methyl ethyl ketone and other polar water-miscible solvents such as dimethylsulfoxide. A preferred solvent system is a mixture of methanol and tetrahydrofuran, at ambient temperature. The cleavage may also be carried out with other bases, including, for example, sodium methoxide, potassium t-butoxide, hydrazine, hydroxylamine, ammonia, alkali metal amides and secondary amines such as diethylamine and the like. In some instances, when very strong bases are used, reaction temperatures in the range of from about 0° to the ambient temperature will give adequately rapid reaction rates.

The hydrolysis step lends itself well to reaction with the base in a 2-phase system with the assistance of a phase transfer catalyst. Such catalysts are now well known and are found among the tetraalkyl ammonium halides and among the crown ethers, such as dicyclohexyl-18-crown-6 ether.

In the case of compounds protected with —COR$_3$ groups, hydrolysis is also readily carried out with acid catalysts, such as methanesulfonic acid, hydrochloric acid, hydrobromic acid, sulfuric acid, a mixture of hydrobromic acid/acetic acid, or with acidic ion exchange resins. Such acid-catalyzed hydrolyses are carried out in hydroxylic solvents, such as water, alkanols, aqueous alkanols, or a mixture of tetrahydrofuran/methanol. It is preferred to carry out such hydrolyses at about the reflux temperature of the mixture, but, when particularly strong acids are used, temperatures as low as the ambient temperature are efficient.

Deprotection of Acylated Dialkoxybenzo[b]thiophene

Where the dialkoxy benzo[B]thiophene is directly acylated (Scheme II) the resulting material may be deprotected to yield the desired dihydroxy final product by treating the acylated dialkoxy material with a sulfur compound chosen from the group consisting of methionine and compounds of the formula

wherein X is hydrogen or unbranched $C_1$-$C_4$ alkyl, and Y is $C_1$-$C_4$ alkyl or phenyl. Alternatively, the deprotection may be conducted by simply adding the sulfur compound to the cyclization reaction mixture without isolation of the cyclized intermediate.

The sulfur compounds are preferably, the alkylthiols, such as methanethiol, ethanethiol, the preferred agent, isopropanethiol, butanethiol and the like; dialkyl sulfides, such as diethyl sulfide, butyl s-butyl sulfide, ethyl propylsulfide, butyl isopropyl sulfide, dimethyl sulfide, methyl ethyl sulfide and the like; benzenethiol; methionine, and alkyl phenyl sulfides such as methyl phenyl sulfide, ethyl phenyl sulfide, butyl phenyl sulfide and the like.

It has been found that the demethylation goes best when a substantial excess amount of the sulfur compound is used, in the range of from about 4 to about 10 moles per mole of the starting benzothiophene. The process can be carried out, although less efficiently, with a smaller amount of the sulfur compound in the range of about 2 or 3 moles per mole of starting compound, and to improve the yield by the addition of about 1 to 3 moles of an alkali metal halide, such as sodium, potassium or lithium chloride, iodide or or bromide. (A similar effect of sodium iodide is shown by Niwa et al., Tet. Let. 22:4239–40 (1981)).

The demethylation reaction goes well at about ambient temperature, in the range of from about 15° to about 30°, and such operation is preferred. However, the demethylation step may be carried out at temperatures in the range of from about −30° to about 50° if it is desired to do so. Short reaction times in the range of about 1 hour have been found to be adequate.

After the product has been demethylated, it is recovered and isolated by conventional means. It is customary to add water to decompose the complex of the acylation catalyst; addition of dilute aqueous acid is advantageous. The product precipitates in many instances, or may be extracted with an organic solvent according to conventional methods.

All of the reaction steps give acceptable yields when the stoichiometric amounts of the reactants are used, except as noted in certain specific steps above. As is normally the case in organic chemistry, improved yields are given by the use of an excess amount of one of the reactants, and it is practical to use an excess amount of the cheaper or the more easily obtained reactant. For example, in the formation of the protected starting compounds, it is practical and economical to use an excess of the acylating or sulfonating agent to assure complete reaction of the more expensive dihydroxy starting compound. Excesses in the range of from about 1% to about 25% are conveniently used, when an excess of one reactant is desired.

The compounds are very often administered in the form of acid addition salts. The salts are conveniently formed, as is usual in organic chemistry, by reacting the compound prepared according to this invention with a suitable acid. The salts are quickly formed in high yields at moderate temperatures, and often are prepared by merely isolating the compound from a suitable acidic wash as the final step of the synthesis. For example, salts may be formed with inorganic or organic acids.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, _-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

All documents, e.g., patents and journal articles, cited above or below are hereby incorporated by reference in their entirety.

The invention is illustrated further by the following examples which are not to be construed as limiting the invention in scope or spirit to the specific procedures described in them. Many of the products were identified by nuclear magnetic resonance (NMR) analysis. Such analyses were run at 100 mHz in deuterochloroform unless stated otherwise.

EXAMPLE 1

6-methoxy-2-(4-methoxyphenyl)benzo[B]thiophene

A 100 g portion of 3-methoxybenzenethiol and 39 g of potassium hydroxide dissolved in 300 ml. of water were added to 750 ml. of denatured ethanol, and the flask was put in a cooling bath. A total of 164 g of a-bromo-4-methoxyacetophenone was then added in small portions, and the mixture was stirred for 10 minutes in the cooling bath after the addition was complete and then for 3 hours at ambient temperature. The solvent was then evaporated off in a vacuum, and 200 ml. of water was added. The mixture was extracted with ethyl acetate, and the organic layer was washed twice with water, twice with aqueous sodium bicarbonate solution, and twice with aqueous sodium chloride solution. The organic layer was then dried over magnesium sulfate, filtered and evaporated under vacuum to obtain 202 g of crude a-(-methoxyphenylthio)-4methoxyacetophenone, which was recrystallized from methanol and washed with hexane to obtain 158 g. of purified product, m.p. 53°.

Alternatively, to a solution of KOH (1.06 g) in 2B-3 ethanol (24 ml) was added dropwise at room temperature over 5 minutes, 3-methoxybenzenethiol (2.26 g). a-(3-methoxyphenylthio)-4-methoxyacetophenone (3.69 g) was added in portions over 20 minutes. 6-methoxy-2-(4-hydroxyphenyl)benzo[b]thiophene and sodium bromide precipatated during the addition of the a-(3-methoxyphenylthio)-4-methoxyacetophenone. HPLC was used to determine the consumption of the starting materials. (Approximate stir time= 1.5 hours.) The reaction was diluted with water (48 ml) and filtered. The product was washed with water (10 ml) and dried overnight in vacuum at room temperature. Yield=4.54 g. (98%) M.P.=52.5°–54° C. Potency=99.3%. (Corrected Yield=97%).

To polyphosphoric acid (41.5 g) was added phosphoric acid (13.8 g) (exotherm to 50° C. observed). a-(3-methoxyphenylthio)-4-methoxyacetophenone (6.92 g) was added steadily over ½ hour. This reaction was heated to 85° C. The reaction is monitored by HPLC for the disappearance of starting acetophenone. Reaction time was 1.75 hours. The reaction was cooled to 50° C. Water (20.7 ml) was added (exotherm to 80° C. observed) causing desired material and 4-methoxy isomer to precipitate (3:1 ratio of 6-isomer to 4-isomer). Toluene (41.5 ml) was added and the reaction heated to >90° C. The aqueous layer was separated and extracted while hot two additional times with toluene (2×20.7 ml). The toluene layers were combined, washed while hot with water (20.7 ml) and concentrated to a volume of 41.5 ml. Upon cooling to 0° C. compound desired 6-isomer preferentially crystallized. The product was collected by filtration, washed with cold toluene (8 ml) and dried in vacuum at 40° C. Yield=13.04 g (69%). M.p.= (shrinks 175° C.) 195°–197° C.

Instead of adding toluene, the following optional workup was utilized in an essentially identical preparation. Water (41.5 ml) was added causing the 6-isomer and 4-isomer compounds to precipitate. The precipitate was filtered and vacuum dried at 40° C. Recrystallization from toluene (41.5 ml) or a slurry in acetone or methanol (41.5 ml) removes the undesired 4-isomer to give pure 6-methoxy-2-(4-hydroxyphenyl)benzo[B]thiophene.

EXAMPLE 1a

Preparation of 6-methoxy-2-(4-methoxyphenyl)benzo[B] thiophene

To polyphosphoric acid (202 g) was added phosphoric acid (67 g). (exotherm to 50° C. observed). a-(-methoxyphenylthio)-4-methoxy acetophenone (20.19 g) was added steadily over ½ hour. The reaction was heated to 85° C. and monitored by HPLC. The reaction is monitored by HPLC for the disappearance of starting acetophenone and 6-methoxy-3-(4-methoxyphenyl)benzo[B]thiophene. Reaction time was 3 hours. The reaction was cooled to 50° C. Water (202 ml) was added (exotherm to 80° C. observed) causing desired product and 4-methoxy-2-(4-methoxyphenyl)benzo[B] thiophene to precipitate at a 3:1 ratio. Toluene (200 ml) was added and the reaction heated to >90° C. The aqueous layer was separated and extracted hot a second time with toluene (200 ml). The toluene layers were combined and concentrated to a volume of 200 ml. Upon cooling to 0° C., the title compound crystallized leaving the 4-methoxybenzothiophene dissolved in toluene. The product was collected by filtration, washed with cold toluene (40 ml) and dried in vacuum at 40° C.

EXAMPLE 2

Deprotection of Dimethoxybenzo[B]thiophene

Ninety g. of pyridine hydrochloride was added to a flask equipped with a distillation head, condenser and collecting flask, and was heated with stirring until the temperature in the distillation head was 220°. The distillation apparatus was then removed, the pot was cooled to 210°, and 30 g. of the above-prepared dimethoxy intermediate was added. The mixture was stirred at 210° for 30 minutes, and was then poured into 250 ml. of ice water. The precipitate was extracted into 500 ml. of ethyl acetate, and the organic layer was washed with 150 ml. of saturated aqueous sodium bicarbonate and then with 150 ml. of saturated aqueous sodium chloride. The organic layer was then dried over magnesium sulfate filtered and evaporated to dryness under vacuum to obtain 25.5 g of the desired intermediate product m.p. >260°.

EXAMPLE 3

6-acetoxy-2-(47acetoxyphenyl)benzo[B]thiophene

Forty g of 6-hydroxy-2-(4-hydroxyphenyl)benzo[B]-thiophene was dissolved in 800 ml. of anhydrous pyridine, and 41.6 g of acetic anhydride and 100 mg. of 4-dimethylaminopyridine were added. The mixture was allowed to stand overnight at ambient temperature, and was then evaporated to an oily residue under vacuum. The residue was slurried with 3 liters of water with vigorous stirring, and the crystals which precipitated were collected by filtration and washed thoroughly with water. The solids were then dried at 80° under vacuum to obtain 52.5 g. of the acetyl-protected intermediate at m.p. 308°–310°.

EXAMPLE 4

6-acetoxy-2-(4-acetoxyphenyl)-3-[4-(2-pyrrolidinoethoxy) benzoyl]benzo[B]thiophene, hydrochloride A 25 g. portion of 4-(2-pyrrolidinoethoxy)benzoic acid, hydrochloride, was converted to its acid chloride by dissolving it in 200 ml. of 1,2-dichloroethane and adding one drop of dimethylformamide and 36.5 g. of thionyl chloride. The mixture was stirred under reflux under a nitrogen blanket for two hours, and was then evaporated under vacuum to obtain the tan-white acid chloride.

To the acid chloride were added 1 liter of 1,2-dichloroethane, 20 g. of b-acetoxy-2-(4-acetoxyphenyl)benzo[B] thiophene and 73.4 g. of aluminum chloride, which last was added over a period of about 3 minutes with vigorous stirring. The mixture was then stirred for one hour, and was poured over 1 liter of ice-water. The layers were separated, and the aqueous layer was extracted three times with 200 ml. portions of water chloroform. The organic layers were combined, dried over magnesium sulfate, filtered and evaporated under vacuum to obtain a yellow oil which was not further purified.

EXAMPLE 5

6-acetoxy-2-(4-acetoxyphenyl)-3-[4(2-piperidinoethoxy) benzoyl]benzo[B]-thiophene, hydrochloride An acylating agent, in acid chloride form, was prepared by combining 26.3 g of 4-(2-piperidino-ethoxy)benzoic acid, hydrochloride, 36.5 g of thionylchloride and 1 drop of dimethylformamide in 200 ml. of 1,2-dichloroethane, and stirring the mixture under reflux for 2 hours under a nitrogen atmosphere. The mixture was then evaporated to dryness under vacuum to obtain the desired 4-(2-piperidinoethoxy) benzoyl chloride, hydrochloride, which was dissolved in 1 liter of 1,2-dichloroethane. To the solution was added 20 g of 6-acetoxy-2-( 4-acetoxyphenyl)benzo[B]thiophene and the mixture was stirred vigorously. To it was then added, over about 3 minutes, 73.4 g of aluminum chloride. During the addition, the reaction mixture turned dark brown and hydrogen chloride evolved. The mixture was then stirred for one hour, and was poured over 1 liter of ice-water. The layers were separated, and the aqueous layer was extracted three times with 200 ml. portions of warm chloroform. The organic layers were combined and dried over magnesium sulfate, and were then filtered and evaporated under vacuum to obtain a brownish-yellow oil, which was not purified. The presence of the desired product was confirmed by thin layer chromatography (TLC) on silica gel, eluting with 9/1 chloroform/methanol, which showed that the major constituent ran at the same R, as authentic 6-acetoxy-2-(4-acetoxyphenyl)- 3-[4(2-piperidinoethoxy)benzoyl]-benzo[B]thiophene.

EXAMPLE 6

6-hydroxy-2- (4-hydroxyphenyl)-3-[4- ( 2-pyrrolidinoethoxy)benzoyl]benzo[B]thiophene 6-acetoxy-2- (4-acetoxyphenyl)-3-[4 (2-pyrrolidinoethoxy)benzoyl]benzo[B]thiophene was added to 275 ml. of methanol. and 55 ml. of 5 N sodium hydroxide was added. The mixture was stirred under reflux for 45 minutes, and the solvent was then removed under vacuum. The residue was dissolved in 300 ml. of methanol, and was extracted twice with diethyl ether. The ether layers were combined, and backwashed with 1 N sodium hydroxide. The aqueous layers were combined and acidified to pH 2–3, and were then made basic to pH 8. The basic solution was then extracted several times with ethyl acetate and the organic layers were combined, dried over magnesium sulfate, filtered and evaporated to a solid under vacuum. After vacuum drying at ambient temperature for several hours, the solid weighed 10.5 g. Analysis by NMR spectroscopy indicated that the product was the desired 6-hydroxy-2-( 4-hydroxyphenyl)-3-[4(2-pyrrolidinoethoxy)benzoyl]benzo[B]thiophene but that approximately an equimolar amount of ethyl acetate was also present. Much of the crude product was used in experimentation on crystallization and purification procedures and so no precise total purified yield was determined. A 1.02 g sample was chromatographed over 8 grams of silica gel using 9/1 ethyl acetate/methanol for elution. The column dimensions were 3×27 cm and 50 ml. fractions were collected. Fractions #13 to 27 provided a yellow oil which was dissolved in 30 ml. of 1 N sodium hydroxide and stirred for 15 minutes at ambient temperature. After acidification with 32 ml. of 1 N hydrochloric acid and basification with excess solid sodium bicarbonate a yellow solid was collected and after vacuum drying overnight it weighed 0.57 g. This material was essentially pure product as judged by NMR and ultraviolet spectral data as well as elemental analysis.

A 10 g portion of the crude product prepared above was chromatographed on a 3×30 cm. column of silica gel, eluting with 1/9 methanol/chloroform. Fifty-ml. samples were collected, and fractions 13–30 were combined and evaporated to dryness to obtain a yellow oil which was dissolved in 30 ml. of 1 N sodium hydroxide. Nitrogen was bubbled through the solution for 15 minutes, and ice and 32 ml. of 1 N hydrochloric acid were added. Then 8 ml. of saturated aqueous sodium bicarbonate was added, and the mixture was stirred for 1 hour and filtered. The solids were washed with water and vacuum dried and a sample was analyzed by 100 mHz NMR in dmso-$d_6$-d1.72 (4H, m, N($CH_2C\underline{H}_2$); 2.68 (4H, m, N($CH_2$ $C\underline{H}_2$)2; 2.94 (2H, t, J=6 Hz,$OCH_2CH_2N$); 4.15 (2H, t, J=6 Hz, $OC\underline{H}_2CH_2N$); 6.68 (2H, d, J=9 Hz, aromatic o to OH); 6.85 (1H, q, $J_{H4-H5=4}$ Hz, $J_{H5-H7}$=2 Hz, H5 of benzothiophene ring); 6.93 (2H, d, J=9 Hz, aromatic o to $OCH_2CH_2N$); 7.18 (2H, d, J=9 Hz, aromatic m to OH); 7.25 (1H, d, J=9 Hz, H4 of benzothiophene ring); 7.67 (2H, d, J=9 Hz, aromatic o to CO); 9.75 (2H, broad 5, OH).

EXAMPLE 7

6-hydroxy-2-(4-hydroxyphenyl)-3-[4-( 2-pyrrolidinoethoxy)benzoyl]benzo[B]thiophene The yellow oil obtained from Example 4 above was dissolved in 700 ml of methanol, and 100 ml. of 5 sodium hydroxide was added. The mixture was stirred for 2 hours at ambient temperature, and then the solvent was removed under vacuum. The residue was dissolved in 500 ml. of water and was washed with two 500 ml portions of diethyl ether. The water layer was acidified to pH 2 with cold methanesulfonic acid, was diluted to about 3 liters, and was washed again with two 1 liter portions of diethyl ether. The aqueous layer was separated, degassed under vacuum, and made basic by addition of sodium bicarbonate. A precipitate developed, and was collected by filtration and washed with water. The solids were vacuum dried at 70° C. to obtain 13 g. of impure product, which was dissolved in 500 ml. of hot acetone, filtered and evaporated down to approximately 100 ml. volume. The solution was cooled and scratched to obtain 11.3 g of product.

From the foregoing it will be appreciated that, although specific embodiments of the invention have been described herein for purposes of illustration, various modifications may be made without deviating from the spirit and scope of the invention.

What is claimed is:

1. A process for preparing compounds of the formula:

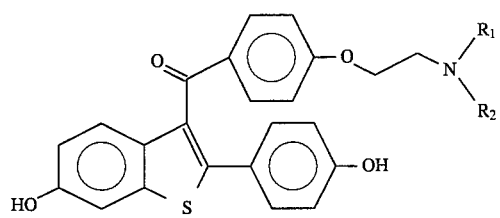

III or the pharmaceutically acceptable salts thereof;

wherein $R_1$ and $R_2$ are independently $C_1$–$C_4$ alkyl, or combine to form $C_4$–$C_6$ polymethylene or —(CH2-)20(CH2)2-;

which process comprises:

cyclizing a compound of the formula

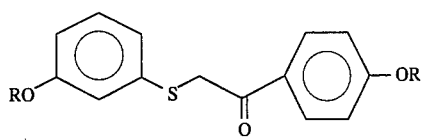

II where the R groups are the same or different and represent Cl-$C_6$ alkyl;

with polyphosphoric acid in the presence of phosphoric acid to yield a mixture of alkoxy-2-(4-alkoxyphenyl) benzo-[B]thiophenes;

optionally removing the alkoxy groups and subsequently reprotecting the hydroxy groups;

acylating the protected benzo[B]-thiophenes under Friedel-Crafts conditions with an acylating agent of the formula:

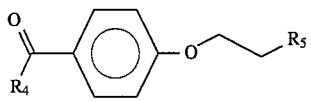

wherein $R_5$ is X or

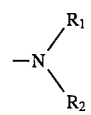

X is chloro, bromo or —$SO_2R^1$;

and $R_4$ is chloro, bromo, iodo, or an activating ester group;

when $R_5$ is X, displacing the X group with an amine of the formula

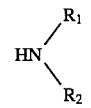

and cleaving the hydroxy protecting groups.

2. A process according to claim 1, wherein R is methyl.

3. A process according to claim 2, wherein the weight ratio of polyphosphoric acid to phosphoric acid is from about 10:1 to 1:1.

4. A process according to claim 3, where $R_5$ is —$N(R_1)(R_2)$.

5. A process according to claim 4, where $R_4$ is chloro.

* * * * *

UNITED STATES PATENT AND TRADEMARK OFFICE
CERTIFICATE OF CORRECTION

PATENT NO.    : 5,523,416

DATED         : June 4, 1996

INVENTOR(S)   : Charles A. Alt

It is certified that an error appears in the above-identified patent and that said Letters Patent is hereby corrected as shown below:

Column 17, lines 34 and 35, delete "-(CH2-) 20(CH2)2-;" and insert -- $-(CH_2-)_2O(CH_2)_2-;$ --.

Column 17, line 45, delete "C1-C6 alkyl;" and insert -- $C_1-C_6$ alkyl; --.

Signed and Sealed this

Twenty-second Day of October, 1996

Attest:

BRUCE LEHMAN

*Attesting Officer*        *Commissioner of Patents and Trademarks*